United States Patent
Sumi et al.

(10) Patent No.: US 9,970,921 B2
(45) Date of Patent: May 15, 2018

(54) METHOD FOR EVALUATING WEATHERING DEGREE OF COAL, METHOD FOR EVALUATING COKING PROPERTY OF WEATHERED COAL, METHOD FOR CONTROLLING WEATHERING DEGREE OF COAL, AND METHOD FOR PRODUCING COKE

(71) Applicant: JFE STEEL CORPORATION, Tokyo (JP)

(72) Inventors: Hiroyuki Sumi, Tokyo (JP); Takashi Anyashiki, Kawasaki (JP); Kiyoshi Fukada, Chiba (JP); Yusuke Dohi, Fukuyama (JP); Hidekazu Fujimoto, Kawasaki (JP); Izumi Shimoyama, Kurashiki (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days. days.

(21) Appl. No.: 14/783,608

(22) PCT Filed: Apr. 8, 2014

(86) PCT No.: PCT/JP2014/002013
§ 371 (c)(1),
(2) Date: Oct. 9, 2015

(87) PCT Pub. No.: WO2014/167843
PCT Pub. Date: Oct. 16, 2014

(65) Prior Publication Data
US 2016/0084816 A1   Mar. 24, 2016

(30) Foreign Application Priority Data
Apr. 12, 2013   (JP) .................................. 2013-083490

(51) Int. Cl.
| | | |
|---|---|---|
| G01N 33/22 | (2006.01) |
| B01F 15/00 | (2006.01) |
| C10B 57/04 | (2006.01) |
| B01F 3/18 | (2006.01) |
| G01N 13/00 | (2006.01) |
| G01N 17/00 | (2006.01) |

(52) U.S. Cl.
CPC ............ *G01N 33/222* (2013.01); *B01F 3/18* (2013.01); *B01F 15/00207* (2013.01); *C10B 57/04* (2013.01); *G01N 13/00* (2013.01); *G01N 17/00* (2013.01)

(58) Field of Classification Search
USPC ................. 366/144; 44/607; 73/788
See application file for complete search history.

(56) References Cited

U.S. PATENT DOCUMENTS 4,135,983 A * 1/1979 Kiritani .................. C10B 57/04
201/21

FOREIGN PATENT DOCUMENTS

| CN | 1965058 A | 5/2007 |
| EP | 2613136 | 7/2013 |
| JP | S54-110897 A | 8/1979 |
| JP | S61191943 A | 8/1986 |
| JP | H06-337265 A | 12/1994 |
| JP | 3302446 | 7/2002 |
| JP | 2005281355 | 10/2005 |
| JP | 2012211332 | 11/2012 |
| KR | 20130079514 | 7/2013 |
| WO | WO 2012/029978 A1 | 3/2012 |

OTHER PUBLICATIONS

Fuerstenau, D.W., et al., "A simple flotation method for rapidly assessing the hydrophobicity of coal particles," 1987, pp. 153-157, vol. 20, International Journal of Mineral Processing.
Fuerstenau, D.W., et al., "Characterization of coal oxidation and coal wetting behavior by film flotation," 1992, pp. 1-17, vol. 10, Nos. 1-4, Coal Preparation (abstract only).
International Search Report for International Application No. PCT/JP2014/002013 dated Jul. 15, 2014.
Journal of the Fuel Society of Japan, 1979, p. 112, vol. 58 (abstract only).
Japanese Office Action for Application No. 2015-511113, dated Jun. 28, 2016, with Concise translation.
Forrest et al., "Theoretical and Experimental Approaches to the Carbonization of Coal and Coal Blends," American Chemical Society, vol. 205, Nov. 12, 1982, pp. 1-25.
Chinese Office Action for Application No. 2014800209034, dated May 3, 2016, with Concise translation.
Fuerstenau, D.W., et al., "Characterization of Coal Oxidation and Coal Wetting Behavior by Film Flotation," Coal Preparation: An International Journal, Taylor & Francis, US, 1992, vol. 10, No. 1, pp. 1-17.

(Continued)

*Primary Examiner* — Prem C Singh
*Assistant Examiner* — Chantel Graham
(74) *Attorney, Agent, or Firm* — RatnerPrestia

(57) ABSTRACT

Provided are, by using an index with which the influence on the strength of coke can be evaluated, a method for evaluating a weathering degree of coal and a coking property of weathered coal within the ranges in which the weathering degree and coking property cannot be determined by using conventional methods, and a method for controlling the weathering degree of coal with which it is possible to add weathered coal to a coal blend to be used for producing coke without decreasing the strength of coke by using the index. The weathering degree of coal is evaluated by using the surface tension of semicoke which is prepared by performing a heat treatment on weathered coal as an index. The weathering degree of each brand of coal is controlled so that the interfacial tension $\gamma_{inter}$ of a semicoke blend which is prepared by blending the plural brands of semicoke in accordance with the proportions is 0.03 mN/m or lower.

8 Claims, 3 Drawing Sheets

(56) References Cited

OTHER PUBLICATIONS

Supplementary European Search Report for Application No. EP 14 78 2384, dated Apr. 4, 2016.
Japanese Office Action with partial English language translation for Application No. 2015511113, dated Jun. 28, 2016, 4 pages.
Korean Office Action with partial English language translation for Application No. 10-2015-7030510, dated Oct. 19, 2016, 5 pages.
U.S. Final Office Action for U.S. Appl. No. 14/388,578, dated Jul. 27, 2017, 11 pages.
U.S. Non Final Office Action for U.S. Appl. No. 14/388,578, dated Feb. 9, 2018, 9 pages.
Niekerk, et al., "Blast-furnace coke: A coal-blending model," Feb. 1991, vol. 91, No. 2, pp. 53-61, Journal of South African Inst. of Mining and Metallurgy.

* cited by examiner

METHOD FOR EVALUATING WEATHERING DEGREE OF COAL, METHOD FOR EVALUATING COKING PROPERTY OF WEATHERED COAL, METHOD FOR CONTROLLING WEATHERING DEGREE OF COAL, AND METHOD FOR PRODUCING COKE

CROSS REFERENCE TO RELATED APPLICATIONS

This is the U.S. National Phase application of PCT/JP2014/002013, filed Apr. 8, 2014, which claims priority to Japanese Patent Application No. 2013-083490, filed Apr. 12, 2013, the disclosures of each of these applications being incorporated herein by reference in their entireties for all purposes.

FIELD OF THE INVENTION

The present invention relates to methods for evaluating a weathering degree of coal which is used as a raw material for coke, methods for evaluating a coking property of weathered coal, methods for controlling a weathering degree of coal, and methods for producing coke.

BACKGROUND OF THE INVENTION

Coke which is used in a blast furnace is required to be sufficiently strong, that is, to have sufficient strength in order to maintain gas permeability in the blast furnace. Since the coke is typically produced by carbonizing in a coke oven a coal blend which is prepared by blending plural brands of coal and the properties of such plural brands of coal strongly influence the strength of coke.

In a steel plant, a coal mine or the like, a coal is stored in a stock yard or etc. until the coal is used. During storage thereof, the coal is subjected to weathering as a result of being exposed to atmospheric air. It is known that the weathering influences properties of coal such as a caking property, amount of heat generation, and coking property of coal in various ways (see Non Patent Literature 1). In addition, it is reported that, in the case where coal (weathered coal) which has been subjected to weathering is added to a coal blend, there is an unexpected decrease in the strength of coke which is produced from such a coal blend (see Non Patent Literature 2). Thus, in the case where a weathered coal is added to a coal blend, there may be an unexpected decrease in strength. Therefore, evaluating the weathering degree of coal which influences the strength of coke has been attempted. Here, "weathering degree of coal" refers to the degree of change in the properties of coal due to weathering, and known examples of a method for evaluating the weathering degree of coal include (A), (B), and (C) below.

(A) Method for determining weathering degree by using a fluidity of coal as an index "Fluidity of coal" refers to a property which is determined by using a method for determining the fluidity of coal by a Gieseler plastometer prescribed in JIS M 8801, in which maximum fluidity MF is used as an index. Since there is a tendency for maximum fluidity MF to decrease with an increase in the number of weathering days, and since maximum fluidity MF is used as one of the factors for controlling the quality of coke, in particular, the strength of coke, maximum fluidity MF has an advantage in that it is used as an index for both weathering degree and strength control (see Non Patent Literature 3).

(B) Method for determining weathering degree by using as an index the chemical composition of a gas which is generated when coal is heated Patent Literature 1 proposes a method in which the weathering degree of coal is determined by using as indices the relationships among the contents of three constituents, that is, $CH_4$, $CO$, and $CO_2$ in a gas which is generated when coal is heated. With this method, it is possible to determine the weathering degree of coal whose MF is equal to or less than the detection limit due to weathering, and it is possible to estimate the amount of decrease in strength.

(C) Method for determining weathering degree by using the surface tension of coal as an index Non Patent Literature 4 reports that it is possible to determine the weathering degree of coal by using as an index the surface tension of unheated coal which is determined by using a film flotation method. Non Patent Literature 4 describes that the surface tension of coal increases as weathering progresses.

PATENT LITERATURE

PTL 1: Japanese Patent Publication No. 3302446

NON PATENT LITERATURE

NPL 1: Journal of the Fuel Society of Japan, vol. 58 (1979), p. 112
NPL 2: Coke Circular, vol. 37 (1988), p. 209
NPL 3: Coke Circular, vol. 23 (1974), p. 88
NPL 4: D. W. Fuerstenau and Jianli Diao: Coal Preparation, vol. 10 (1992), p. 1 to 17

SUMMARY OF THE INVENTION

Although the methods as (A) through (C) described above have been proposed as index for evaluating weathering degree in consideration of influence on the strength of coke, the methods have problems as described in followings.

In the case of the method (A), a measuring machine used in the method is in wide spread use, and it is easy to perform measuring. However, since there is a detection limit for the measurement value of maximum fluidity MF, there is a problem in that it is difficult to determine the weathering degree of coal having a low maximum fluidity. Because maximum fluidity MF decreases due to weathering and becomes 0 when weathering has progressed to some extent, which makes it difficult to continue determining weathering degree. In addition, maximum fluidity MF is an important blending index like the mean maximum reflectance Ro of vitrinite in coal and a parameter useful to estimate the strength of coke. However, in the case where weathered coal is blended, since the correlation, which is established between the strength of coke and mean maximum reflectance Ro of vitrinite in coal and/or maximum fluidity MF in the case where weathered coal is not blended, is not established, and since the strength of coke is widely different from (lower than) that estimated from the correlation, there is also a problem, in particular, in that maximum fluidity MF cannot be used as a blending index in the case where weathered coal is blended.

According to the method (B), it is possible to determine the weathering degree of coal having a low maximum fluidity MF and the amount of decrease in the strength of coke. However, since a technique for estimating the amount of decrease in the strength of coke is disclosed only with a result in the case where one kind of coal is carbonized, and since there is no mention of estimating strength in the case where plural kinds of coal are blended as is the case with a practical operation, there is a problem in that the result in the case of a coal blend is not clear.

In the case of the method (C), although it is described that there is a correlation between the weathering degree of coal and the surface tension of coal, since there is no mention of the influence of weathering degree on the change in surface tension and the strength of coke in the case where the coal is carbonized, it is difficult to evaluate the coking property of weathered coal in the case where the weathered coal is used for producing coke. Here, "coking property" refers, in the case where coke is produced from coal, to the quality of increasing or decreasing the strength of coke as a result of the coal being used for producing the coke.

The present invention has been completed in view of the situation described above, and an object of the present invention is to provide, by using an index with which the influence on the strength of coke can be evaluated, methods for evaluating the weathering degree of coal and/or the coking property of weathered coal, e.g., within the ranges in which the weathering degree and coking property cannot be determined by using conventional methods and/or methods for controlling the weathering degree of coal with which it is possible to add weathered coal to a coal blend to be used for producing coke without decreasing the strength of coke by using the index.

Aspects of the present invention may solve the problems described above as follows.

[1] A method for evaluating a weathering degree of coal including using surface tension of semicoke which is prepared by performing a heat treatment on a weathered coal as an index for evaluating the weathering degree.

[2] A method for evaluating a coking property of weathered coal when coke is produced from coal blend including the weathered coal comprising using surface tension of semicoke which is prepared by performing a heat treatment on the weathered coal as an index for evaluating an amount of decrease in a strength of the coke due to weathering.

[3] A method for controlling a weathering degree of coal by using the method according to the item[1] including steps of: previously determining surface tension of each brand of semicoke which is prepared by performing a heat treatment on each of plural brands of coal included in coal stock and previously assessing a proportion of each of the plural brands of coal in the coal stock; and in a condition the plural brands of semicoke are blended in accordance with the respective proportions to prepare a semicoke blend, controlling the weathering degree of each of the plural brands of coal so that a value of interfacial tension $\gamma_{inter}$ of the semicoke blend which is derived from the surface tensions and the proportions is 0.03 mN/m or lower.

[4] A method for controlling a weathering degree of coal by using the method according to the item[1] including steps of: previously determining surface tension of each brand of semicoke which is prepared by performing a heat treatment on each of plural brands of coal included in coal stock and previously assessing a proportion of each of the plural brands of coal in the coal stock; and controlling the weathering degree of a control target brand of coal included in the coal stock so that a difference $\Delta\gamma$ in surface tension regarding a semicoke is 1.5 mN/m or lower, the difference $\Delta\gamma$ being between value of surface tension of the semicoke which is prepared by performing a heat treatment on the control target brand of coal and weighted average value which is calculated by weighted averaging surface tensions of the brands of semicoke which are prepared by performing a heat treatment on remaining brands of coal other than the control target brand of coal included in the coal stock according to proportions of the remaining brands of coal.

[5] A method for controlling a weathering degree of coal by using the method according to the item[1] including controlling the weathering degree of a control target brand of coal so that a semicoke which is prepared from the weathered control target brand of coal has surface tension corresponding to 39.5 mN/m or higher, the value 39.5 mN/m being surface tension of the semicoke which is prepared by performing a heat treatment at a temperature of 500° C. on the weathered brand of coal.

[6] A method for producing coke including steps of: preparing a coal blend by blending the brands of coal whose weathering degrees have been controlled by using the methods according to any one of the items [3] to [5]; and producing coke by carbonizing the coal blend.

According to aspects of the present invention, by using the surface tension of the semicoke which is prepared by performing a heat treatment on weathered coal as an index for weathering degree of coal, it is possible to evaluate the weathering degree of the coal even within the range in which weathering degree cannot be determined by using conventional methods. This evaluation makes it possible to produce coke while controlling the weathering degree of coal to be within the range in which a decrease in the strength of the coke can be suppressed. Accordingly, it is possible to add weathered coal to a coal blend which is made into coke having desired strength.

DETAILED DESCRIPTION OF EMBODIMENTS OF THE INVENTION

Figure 1:
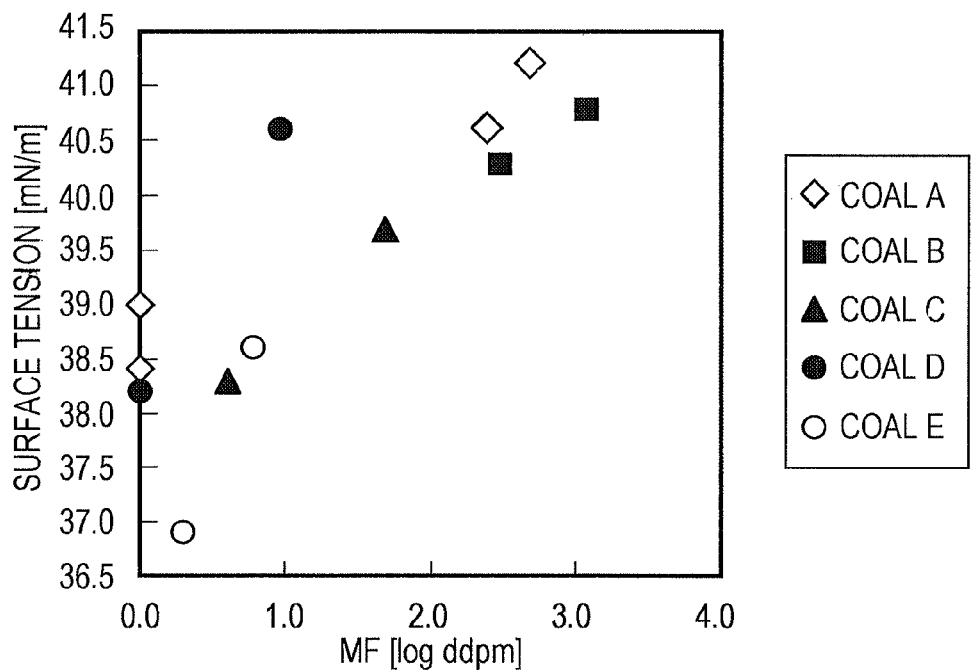
FIG. 1 shows a graph illustrating the relationship between the maximum fluidity MF of each of various brands of coal and the surface tension of semicoke which is prepared by performing a heat treatment on each of the various brands of coal.

Semicoke may be prepared by performing a heat treatment on coal. Although the semicoke has not drawn much attention in conventional coke producing techniques, the present inventors focuses on the semicoke to find that it is possible to evaluate the adhesiveness between two kinds of coal on the basis of the difference in surface tension between the two kinds of the semicoke or on the basis of the interfacial tension of the semicoke.

Moreover, the present inventors focus on a phenomenon in which if a weathered coal is added to a coal blend, there may be an unexpected decrease in the strength of coke which is obtained by carbonizing the coal blend. The present inventors diligently conduct investigations regarding the phenomenon and finding described above to find that it is possible to evaluate the weathering degree of coal in a mixture of plural brands of coal by using the surface tension of the semicoke which is prepared from each of plural brands of coal as an index. In addition, the present inventors found that it is possible to control the strength of coke by evaluating the amount of decrease in the strength of coke due to weathering and by controlling the weathering degree of coal by using the index described above or the interfacial tension of a semicoke blend which is prepared by blending plural brands of semicoke.

Generally, it is known that, in the case where two kinds of materials having different surface tensions are adhered to each other, adhesion strength increases with decreasing difference in surface tension. In a process in which coal is made into coke, coal melts first due to heating and re-solidifies to form coke. In such a process, the two kinds of coal adhere to each other to form a strong coke structure. To date, it has been considered that, since such an adhesion structure is formed as a result of the fusion of coal particles, the plastic property (such as maximum fluidity MF) of coal plays an important role. In contrast, since the present inventors, focusing on a phenomenon in which different kinds of coal adhere to each other, thought that the adhesion strength may influence the strength of coke in some way, the present inventors conducted investigations regarding the adhesion phenomenon, and as a result, empirically established the relationship between a difference in surface tension and the strength of coke.

In the case where the adhesion phenomenon described above is investigated, it is considered to be preferable to use the surface tension of coal plastics which is determined in a temperature range (350° C. to 800° C.) in which coal particles start to soften, adhere to each other, and solidify to form coke in a practical process. Because it is considered that the adhesion strength between coal particles is influenced by the surface tension of softened coal plastics from when softening starts until coke is formed. Therefore, it is presumed to be preferable to determine the surface tension of coal realizing the adhesion strength in this temperature range.

However, a method for determining the surface tension of a material in such a high temperature range is not known. Therefore, the present inventors experimented with various alternative methods to find that it is possible to express the adhesion strength between coal particles by using the surface tension of heat-treated coal which has been subjected to a heat treatment in which the coal is first heated and then cooled to room temperature, preferably rapidly cooled, and that such an adhesion phenomenon influences the strength of coke. Such heat-treated coal is called semicoke, and specifically the semicoke is a heat-treated coal which has been heated in a temperature range (350° C. to 800° C.) in which coal particles start to soften, adhere to each other, and solidify to form coke and which has been cooled. The present inventors presumed that it is possible to evaluate the weathering degree of coal which influences the adhesion strength of coke by using the surface tension of semicoke as an index for the evaluation.

Generally, since interfacial tension can be calculated from surface tension, the present inventors diligently conducted experiments on the basis of the presumption described above to specifically clarify that, in the case where the interfacial tension of a semicoke blend, which is prepared from a coal mixture composed of plural brands of coal, is higher than 0.03 mN/m, there is a decrease in the strength of coke which is obtained by carbonizing the coal mixture. In the case where the number of brands of coal which are subjected to a heat treatment is n and where the number of brands of semicoke of which a semicoke blend is composed is n, the interfacial tension $\gamma_{inter}$ of the semicoke blend can be expressed by the following relational expression in terms of matrixes W and Γ.

Math. 1

$$\gamma_{inter} = W \Gamma W^a \quad (1)$$

Here, in the case where the number of brands of coal of which a coal mixture is composed is n, matrixes W and Γ are expressed by the relational expressions below in terms of the blending ratio $w_i$ of an i-th coal, that is coal i, and the interfacial tension $\gamma_{ij}$ between semicoke i, which is prepared from the i-th coal i, and semicoke j, which is prepared from a j-th coal, that is coal j. It is primarily preferable that a blending ratio $w_i$ be indicated by the blending ratio of semicoke in a semicoke mixture which is prepared from a coal mixture. However, since there is not a large difference between the content of each brand of semicoke in a semicoke mixture and the content of each brand of coal in a coal mixture even after a heat treatment has been performed, $w_i$ is indicated in terms of the blending ratio of each coal in a coal mixture.

Math. 2

$$\Gamma = \begin{pmatrix} \gamma_{11} & \gamma_{12} & \cdots & \gamma_{1j} & \cdots & \gamma_{1n} \\ \gamma_{21} & \gamma_{22} & & & & \vdots \\ \vdots & & \ddots & & & \vdots \\ \gamma_{i1} & & & \gamma_{ij} & & \gamma_{in} \\ \vdots & & & & \ddots & \vdots \\ \gamma_{n1} & \cdots & \cdots & \gamma_{nj} & \cdots & \gamma_{nn} \end{pmatrix} \quad (2)$$

Math. 3

$$W = (w_1 w_2 \ldots w_i \ldots w_n) \quad (3)$$

In addition, in the case where the number of brands of coal of which a coal mixture is composed is n, since the total blending ratio of all the constituent brands of coal is 1, the following relational expression is satisfied.

Math. 4

$$\sum_{i=1}^{n} w_i = 1 \quad (4)$$

Regarding the interfacial tension $\gamma_{ij}$ in relational expression (2), $\gamma_{ij} = \gamma_{ji}$ is satisfied by definition thereof. The interfacial tension $\gamma_{ij}$ between two brands of semicoke is expressed by the following relational expression in terms of the surface tension $\gamma_i$ of semicoke i and the surface tension $\gamma_j$ of semicoke j on the basis of the relational expression by Li and Neumann.

Math. 5

$$\gamma_{ij} = \gamma_i + \gamma_j - 2\exp[-\beta(\gamma_i - \gamma_j)^2]\sqrt{\gamma_i \gamma_j} \quad (5)$$

Here, constant β is 0.0001247 $(m^2/mJ)^2$.

By using relational expression (6) below, which is derived by simplifying relational expression (1) by using the variance $\sigma_\gamma^2$ of the surface tension of a semicoke blend, the value of the interfacial tension of semicoke can be calculated. The value of interfacial tension $\gamma_{inter}$ calculated by using relational expression (6) above is almost equal to the value calculated by using relational expression (1), and there is no practical problem due to the difference.

Math. 6

$$\gamma_{inter} = 0.032 \sigma_\gamma^2 \qquad (6)$$

The variance $\sigma_\gamma^2$ in relational expression (6) can be calculated by using relational expression (7) below.

Math. 7

$$\sigma_\gamma^2 = \frac{100}{100 \sum_{i=1}^{n} w_i - 1} \left[ \sum_{i=1}^{n} \gamma_i^2 w_i - \frac{\left( \sum_{i=1}^{n} \gamma_i w_i \right)^2}{\sum_{i=1}^{n} w_i} \right] \qquad (7)$$

In addition, the interfacial tension of a semicoke blend decreases with decreasing differences in surface tension among plural brands of semicoke which are prepared from plural brands of coal, and the interfacial tension increases with increasing differences in surface tension. Therefore, in order to prevent the strength of coke from decreasing, it is preferable to blend brands of coal which become brands of semicoke having surface tensions close to each other. In consideration of this, the present inventors diligently conducted investigations and experiments, and as a result, also found that, in the case where the difference in surface tension among brands of semicoke is used as an index, when the difference Δγ in surface tension between the semicoke which is prepared from a coal mixture composed of one or plural brands of coal selected from among all the plural brands of coal and the semicoke which is prepared from the remaining brands of coal other than the brands of coal used for the coal mixture among all the plural brands of coal is higher than 1.5 mN/m, there is a significant decrease in the strength of coke which is prepared from all the plural brands of coal. In the present invention, even if the number of the brands of coal of which the coal mixture is composed is not plural but one, the coal mixture is called "mixture" for descriptive purposes.

Hereafter, the surface tension of semicoke will be described. First, a method for preparing semicoke will be described. It is appropriate that a temperature at which coal is heated in order to prepare semicoke be in a temperature range in which coal particles are heated to start softening, adhere to each other, and solidify to form coke, that is, from a temperature equal to or higher than 350° C., at which coal particles start to soften, to a temperature equal to or lower than 800° C., at which coking is completed. Therefore, it is preferable that semicoke be prepared by heating the coal at a temperature of 350° C. or higher and by then cooling the coal in an atmosphere sealed from the air or in an atmosphere of an inert gas. Since a temperature which contributes particularly to adhesion within the heating temperature range of 350° C. or higher and 800° C. or lower is a temperature at which softening is occurring, since a temperature range in which softening of coal is occurring in a coke producing process is 350° C. or higher and 550° C. or lower, and since it is considered that an adhesion structure is determined at a temperature of about 500° C., it is preferable that the heating temperature be about 500° C., that is, 480° C. or higher and 520° C. or lower. That is to say, it is preferable that the heating temperature for treating weathered coal in order to prepare semicoke be 350° C. or higher and 800° C. or lower, more preferably 350° C. or higher and 550° C. or lower, or most preferably 480° C. or higher and 520° C. or lower.

Coal is cooled in an atmosphere of an inert gas in order to decrease the measurement error of surface tension, because, since coal has a high temperature immediately after heating has been performed, a structural change occurs due to partial oxidization on the surface of coal in the case where cooling is performed in an atmosphere containing oxygen, which results in the measurement error of surface tension. A rare gas such as helium gas or argon gas or nitrogen gas may be used as an inert gas, and it is appropriate that nitrogen gas be used.

Moreover, it is preferable that coal be rapidly cooled after heating has been performed. Heated coal is rapidly cooled in order to maintain a molecular structure which has been formed in the softened state, and it is preferable that cooling be performed at a cooling rate of 10° C./sec or more at which it is considered that the molecular structure does not change. Although examples of a rapid cooling method include a method using a liquid such as liquid nitrogen, iced water, or water or an inert gas such as nitrogen gas, since gas cooling takes a long time to cool the inside of coal and causes variations in cooling rates, and since cooling with iced water or water influences the results of the measurement of surface tension due to the adhesion of water, it is preferable that rapid cooling be performed by using liquid nitrogen. Specifically, it is appropriate that a vessel containing coal be dipped into liquid nitrogen.

An exemplary, non-limiting method for performing a heat treatment on coal in the present invention is as follows.

(a) Coal is pulverized. It is preferable that coal be pulverized to a particle diameter of 250 μm or less in accordance with the proximate analysis of coal prescribed in JIS M 8812.

(b) The coal pulverized in process (a) is heated at an appropriate heating rate. It is preferable that the heating rate be determined in accordance with the heating rate at which coke to be evaluated by using surface tension and interfacial tension is produced. It is appropriate that the coal be heated to a temperature of 350° C. or higher and 800° C. or lower as described above.

(c) The coal heated in process (b) is cooled with liquid nitrogen. It is preferable that rapid cooling be performed by using the method described above.

Hereafter, a method for determining surface tension will be described. Known examples of a method for determining surface tension include a sessile drop method, a capillary-rise method, a maximum bubble pressure method, a pendant drop method, a drop weight method, a plate method (Wilhelmy method), an advancing/receding contact angle method, a ring method, a tilting plate method, a retention time measurement method, a film flotation method, and the like. Since coal is composed of various molecular structures, it is presumed that the surface tension of coal is not uniform. Therefore, it is particularly preferable that a film flotation method (D. W. Fuerstenau; "International Journal of Mineral Processing, 20 (1987), p. 153.) be used, because it is expected that the surface tension distribution can be evaluated.

Hereafter, various conditions for the determination of surface tension by using a film flotation method will be described. Since the value of the surface tension of coal is distributed in a range of 20 to 73 mN/m at room temperature and when softening is occurring, it is appropriate that a liquid having a surface tension in this range be used in a film flotation method. It is possible to prepare a liquid having a surface tension of 20 to 73 mN/m from an aqueous solution of an organic solvent such as ethanol, methanol, propanol, tert-butanol, or acetone. It is possible to determine the surface tension distribution of a sample by dropping sample particles onto various kinds of liquids having various surface tensions, by determining the proportion in terms of the mass of floating sample particles for each kind of liquid, and by representing the results in the form of a frequency distribution curve. As for the diameter of the sample particles whose surface tension is to be determined, since it is preferable to determine surface tension when the contact angle of the object sample with the liquid is almost 0°, and since the contact angle increases with an increase in the diameter of the pulverized sample particle, it is preferable that the particle diameter be as small as possible. However, since the particles tend to aggregate in the case where the diameter of sample particles is less than 53 μm, it is preferable that the sample be pulverized so that the diameter of sample particles is 53 to 150 μm to prevent the aggregation.

Since a film flotation method utilizes the flotation phenomenon of a material (sample particles) due to surface tension, it is preferable that measurement be conducted under the condition that the gravity of the material is negligible. Because there is an increase in contact angle due to the influence of gravity in the case where the density of the material is high. Therefore, the surface tension preferably measured regarding a material having a density of 2000 kg/m$^3$ or less with which it is considered that a contact angle is not influenced by gravity. Since various kinds of coal and semicoke satisfy this condition, it is possible to use powdered coal and semicoke of all kinds as sample particles for a film flotation method and determine by the method the surface tension of all kinds of coal such as hard coking coal, non- or slightly-caking coal, and anthracite regardless of the kinds of coal. Moreover, it is also possible to measure the surface tension of additives such as pitch, oil coke, coke breeze, dust, waste plastics, and biomass in the same way.

An example of a method for preparing samples of coal which are used for a film flotation method will be described in the following processes.

(a') Coal is pulverized to a particle diameter of 200 μm or less.

(b') The coal which has been pulverized in process (a') is heated to a temperature of 500° C. at a heating rate of 3° C./min in an inert gas flow. The heating rate in process (b') above is determined to be 3° C./min, because the heating rate is 3° C./min when coke is produced in a coke oven.

(c') The coal heated in process (b') is rapidly cooled with liquid nitrogen.

(d') The coal rapidly cooled in process (c') is pulverized to have a particle diameter of 150 μm or less, and the pulverized coal is dried at a temperature of 120° C. for 2 hours in a dried inert gas flow. Any kind of drying method may be used in process (d') as long as water adhering to the surface of the particles is removed, and a method in which drying is performed under a decompressed condition may be used in addition to a method in which heating is performed to a temperature of 100° C. to 200° C. in an inert gas such as nitrogen or argon.

Examples of an index of the surface tension of semicoke include the average value of surface tension distribution (average surface tension), the standard deviation of surface tension distribution, the surface tension of a peak value in surface tension distribution, two values of the maximum surface tension and the minimum surface tension in surface tension distribution, and the distribution function of surface tension distribution. The average value of surface tension distribution (the average value of γ) is expressed by, for example relational expression (8) below. The value of the surface tension of semicoke may be indicated as the average value of surface tension distribution, a value which is considered to be highly accurate among plural determined values of surface tension, or the average value of such determined values. It is most preferable that the surface tension of semicoke in a non-limiting embodiment of a method of the present invention be indicated by the average value of surface tension distribution which is derived by using a film flotation method.

Math. 8

$$\vec{\gamma} = \int \gamma f(\gamma) d\gamma \qquad (8)$$

Here, γ with an overbar: average value of surface tension distribution;
γ: surface tension; and
f(γ): frequency of surface tension distribution.

The present inventors measured the surface tension of the semicoke which was prepared by performing a heat treatment at a temperature of 500° C. on a brand of coal to be used for producing coke among brands of coal which had not been weathered. From the measurement results, the surface tension of the semicoke determined by using the method described above was 37.0 to 45.0 mN/m with a measurement error of 0.4 mN/m. Such values of surface tension and measurement error are related to the average value of the surface tension distribution of semicoke determined by using the method described above, and, hereinafter, the value given as a surface tension refers to the average value of the surface tension distribution described above, unless otherwise noted.

Hereafter, a change in the surface tension of semicoke due to weathering will be described. As described above, the present inventors clarified with experiments, in addition to the surface tension of semicoke influencing adhesion of coal, not only that the surface tension of semicoke influences the adhesion of coal but also that the surface tension of semicoke is decreased due to weathering.

EXAMPLES

Coal A through coal E which were used in the present experiments and the properties of the brands of coal and the brands of semicoke which were prepared from the brands of coal are given in Table 1. Such brands of semicoke were prepared by using the processes (a') through (d') above.

TABLE 1

| Coal Name | γ [mN/m] | Ro [—] | MF [logddpm] | Ash [%, d.b.] | VM [%, d.b.] |
|---|---|---|---|---|---|
| Coal A$_0$ | 41.2 | 0.99 | 2.68 | 8.5 | 28.0 |
| Coal A$_1$ | 39.0 | 0.99 | ND | | |
| Coal A$_2$ | 38.4 | 0.99 | ND | | |
| Coal A$_3$ | 40.6 | 0.99 | 2.38 | | |
| Coal B$_0$ | 40.8 | 1.08 | 3.07 | 9.2 | 24.3 |
| Coal B$_1$ | 40.3 | 1.08 | 2.47 | | |
| Coal C$_0$ | 39.7 | 1.14 | 1.68 | 9.4 | 23.2 |
| Coal C$_1$ | 38.3 | 1.14 | 0.60 | | |
| Coal D$_0$ | 40.6 | 1.59 | 0.95 | 12.5 | 16.8 |
| Coal D$_1$ | 38.2 | 1.59 | ND | | |
| Coal E$_0$ | 38.6 | 1.62 | 0.78 | 9.4 | 17.1 |
| Coal E$_1$ | 36.9 | 1.62 | 0.30 | | |

ND: not dilatated (MF = 0 ddpm)

In the present experiments, the present inventors investigated the relationship between the weathering degrees of coal A through coal E and the surface tensions of the brands of semicoke which were respectively prepared from coal A through coal E. Among the coal names in Table 1, the one with suffix 0 indicates coal before weathering was performed, the one with suffix 1 indicates coal which had been subjected to accelerated weathering at a temperature of 150° C. for 3 hours being heated in air atmosphere, and the one with suffix 2 indicates coal which had been subjected to accelerated weathering at a temperature of 150° C. for 5 hours being heated in air atmosphere. In particular, in the case of coal A, the one with suffix 3 indicates coal A which had been subjected to spontaneous weathering for 3 months in atmospheric air.

In addition, the present inventors determined the maximum fluidity MF of each of the coal named in Table 1 and the surface tension of the semicoke which was prepared from each of the named coals. The determination results are given in FIG. 1. In FIG. 1, a measurement value of a MF of 0 ddpm is indicated by a point on the line for a log MF of 0. The surface tension γ [mN/m] in Table 1 indicates the value of the surface tension of the semicoke which was prepared from the corresponding coal listed in the "Coal Name" column. The value of the surface tension represents the average value of the surface tension distribution which was obtained by using a film flotation method as described above.

In Table 1, the mean maximum reflectance Ro of vitrinite in coal and maximum fluidity MF for each coal name are given. As described in "(A) Method for determining weathering degree by using the fluidity of coal as an index" in Background Art, maximum fluidity MF is one of the indices for determining weathering degree. It is known that, as the weathering of coal progresses, the maximum fluidity MF of the coal decreases. The mean maximum reflectance Ro of vitrinite in coal in Table 1 is given for reference. The Ash value and the VM value in Table 1 are values determined for coal before weathering was performed, and a change in the Ash value or VM value due to weathering was not observed. Here, the values of Ash and VM in Table 1 are based on dry weight and expressed in units of [%, d.b.] in Table 1.

As FIG. 1 indicates, it is clarified that, in the case of the same brand of coal, as maximum fluidity MF decreases due to weathering, the surface tension of the semicoke which is prepared from the weathered coal decreases. From the results for coal name $A_3$, it is clarified that there is a decrease in surface tension due to spontaneous weathering as is the case with weathering due to accelerated weathering through heating. Therefore, it is clarified that, by determining surface tension at a base point in time when the evaluation of weathering degree is started, for example, immediately after the start of storing, and by determining surface tension at a time when weathering degree is to be evaluated, it is possible to quantitatively assess weathering degree.

Since a tendency for the surface tension of semicoke, which is prepared by heating the coal, to decrease as weathering progresses is the opposite of a change in the surface tension of unheated coal to increase as weathering progresses as reported in Non Patent Literature 4, it is clarified that the experimental results described above cannot be inferred from the results of Non Patent Literature 4.

In the case where maximum fluidity MF is used as an index of weathering degree, after MF has decreased to 0 ddpm (detection limit) due to weathering, it is not possible to evaluate the weathering degree of the coal even if the weathering of the coal further progresses. On the other hand, in the case where the weathering degree of coal is evaluated by using the surface tension of semicoke as an index, it is possible to detect the difference in weathering degree between named coals $A_1$ and $A_2$ which have a maximum fluidity MF of 0 ddpm.

As described above, the present inventors clarified that the surface tension γ of semicoke correlates with the weathering degree of coal through the maximum fluidity MF of the coal. From this clarification, it is presumed that the interfacial tension of semicoke, which is calculated from the surface tension of semicoke, correlates with the weathering degree of coal.

To date, it has been reported that there is an unexpected decrease in strength due to weathered coal being blended. This is considered to be caused by the strong influence of a decrease in surface tension due to weathering. The present inventors conducted additional experiments regarding a decrease in the strength of coke which is obtained by carbonizing a coal blend which is prepared by blending weathered coal. As a result of the experiments, the present inventors found a relationship between the interfacial tension of semicoke and the strength of coke in which there is a significant decrease in the strength of coke in the case where the interfacial tension of the semicoke which is prepared from the coal blend is higher than 0.03 mN/m. The present inventors focused on this relationship to think that there is a relationship between the strength of coke and the difference in surface tension between two kinds of semicoke where one of them is prepared from weathered brands of coal and the other is prepared from the remaining brands of coal for a coal blend other than the weathered brands of coal, and there is a significant decrease of the strength of coke in the relationship in the case where the difference in surface tension is higher than a certain threshold value. Thus, the present inventors conducted further additional experiments, and as a result, clarified that there is a significant decrease in the strength of coke in the case where the difference in surface tension between the two kinds of semicoke is higher than 1.5 mN/m. Moreover, the present inventors considered about the presence of the threshold value for a difference in the surface tension of semicoke and considered that there is also such a threshold value for the surface tension of semicoke, and conducted further additional experiments. As a result, the present inventors found that, in the case where the value of the surface tension of the semicoke which is prepared by performing a heat treatment at a temperature of 500° C. is 39.5 mN/m, this is an indicative value at which there is a decrease in the strength of coke.

From the considerations and the results of the additional experiments, in order to blend and use weathered coal without decreasing the strength of coke, it is clarified that it is appropriate that the weathered coal be blended and used so that the interfacial tension of the semicoke which is prepared from the coal blend is not higher than 0.03 mN/m, or so that the difference in surface tension between the two kinds of semicoke which are prepared from the weathered brands of coal and the remaining brands of coal is not higher than 1.5 mN/m. In addition, it is also clarified that it is appropriate that weathered coal from which semicoke having a surface tension corresponding to a value of 39.5 mN/m or higher. The value of 39.5 mN/m means the surface tension of the semicoke which is prepared by performing a heat treatment at a temperature of 500° C. on the weathered coal be used for the coal blend. Here, some of the additional experiments are described in EXAMPLE 1 below, and the preferable threshold value and the preferable value described above are illustrated in FIGS. 2 through 4.

In the case of single coal, although it is possible to derive the threshold value of the surface tension of semicoke, which influences the strength of coke, based on the results of a carbonizing test as described in EXAMPLE, it is also possible to obtain the threshold value by calculation. For example, under the assumption that brands of coal to be contained in a coal blend for producing coke are decided, focusing on a certain brand of coal among the brands of coal to be contained in the coal blend, in the case where the value of the surface tension of the semicoke which is prepared from the target brand of coal is varied due to the weathering of the target brand of coal, it is possible to calculate the value of the interfacial tension of a semicoke blend which is prepared from the coal blend. By calculating the interfacial tension of common coal blends for producing coke by using the method described above, it was clarified that, in the case where the value of the surface tension of the semicoke which is prepared by performing a heat treatment at a temperature of 500° C. on the target brand of coal is lower than 39.5 mN/m, the interfacial tension of the semicoke blend is generally higher than 0.03 mN/m. Therefore, in the case where there is a decrease in the surface tension of semicoke due to weathering, if the semicoke has a surface tension of 39.5 mN/m or higher in terms of the surface tension of the semicoke which is prepared by performing a heat treatment at a temperature of 500° C. on the weathered coal, since the interfacial tension of the semicoke blend is 0.03 mN/m or lower, it is thought to be possible to add the coal from which the semicoke is prepared to the coal blend without decreasing the strength of coke which is obtained by carbonizing the coal blend.

Method for Controlling the Weathering Degree of Coal

As described above, in the case where there is a decrease in the surface tension of the semicoke which is prepared from a certain brand of coal which has been subjected to weathering, there is an increase in the difference in surface tension between the semicoke and the semicoke which is prepared from brands of coal other than the weathered brand of coal, and as a result, there is a decrease in the strength of coke which is obtained by carbonizing the coal blend containing the weathered brand of coal. Therefore, in order to prevent a decrease in surface tension due to weathering while being stocked for the purpose of preventing a decrease in the strength of coke, it is preferable to control the weathering degree of coal to be within a certain limit. The present inventors conducted various investigations regarding a method for controlling a decrease in surface tension due to weathering by using the surface tension or interfacial tension of semicoke described above as an index.

There is a fact that a decrease in the strength of coke due to the weathering of coal is caused by the difference in surface tension between the brands of coal when softening occurs. This fact indicates the possibility that there is a difference in surface tension between the semicoke which is prepared from the weathered brand of coal contained in the coal blend and the semicoke which is prepared from brands of coal contained in the coal blend other than the weathered brand of coal and that the difference plays an important role. For example, there is the case where weathered brand of coal which is a source of semicoke which causes a decrease in surface tension due to weathering, is added to a coal blend as a raw material for coke. If the surface tension of the semicoke which is prepared from the remaining brands of coal in the coal blend other than the weathered brand of coal is close to the surface tension of the semicoke which is prepared from the weathered brand of coal, a decrease in the strength of coke is less likely to occur. Therefore, in order to decide a control value of the surface tension of the semicoke which is prepared from weathered brand of coal, it is appropriate to consider the surface tension of the semicoke which is prepared from each of the brands of coal which are used in combination with the weathered brand of coal.

The method for controlling the weathering degree of coal according to an aspect of the present invention is based on the assumption that the weathering degree of coal is controlled when the coal is stored, for example, in a stock yard. That is to say, since weathering of coal spontaneously progresses in atmospheric air, it is possible to prevent a decrease in the strength of coke over the long term, for example, in the case where it is possible to control the weathering degree of each brand of coal and to use a weathered brand of coal before the weathering degree reaches the limit. In the case of the method for controlling weathering degree according to an aspect of the present invention, the surface tension of each brand of semicoke which is prepared from each of the brands of coal included in coal stock which can be used for producing coke may be determined in advance (previously). In addition, the proportion of each brand of coal to the whole coal stock may be previously assessed in order to control the weathering degree of the brand of coal. "Coal stock" refers to coal stored in a storage place such as a stock yard, and, usually, plural brands of coal are stored in the storage place. In addition, "the proportion of each brand of coal to the whole coal stock" refers to the abundance ratio of each brand of coal in the coal stock. Here, in the case of coal which is scheduled to be stored, if the surface tension of the semicoke which is prepared from the coal and the amount of the coal stored are known, the coal may be treated as a part of the coal stock.

Examples of a method for determining the surface tension distribution include a method in which a surface tension distribution is obtained by determining the surface tension of semicoke by using the film flotation method described above, a method in which a surface tension distribution is obtained by using the values of surface tension determined by a third party using the film flotation method or the other method, and a method in which a surface tension distribution is obtained from a third party.

In the present invention, specifically, it is preferable that the weathering degrees of plural brands of coal included in coal stock be controlled by using as indices the interfacial tensions or surface tensions of plural brands of semicoke which are prepared from the plural brands of coal and by using exemplary controlling methods (1) through (3) described below. Although it is assumed that 10 brands of coal are included in coal stock in controlling methods (1) through (3) below, there is no particular limitation on the number of brands of coal included in coal stock in the present invention.

Controlling Method (1)

[1i] One brand of coal whose weathering degree is to be controlled is selected from among 10 brands of coal included in coal stock.

[1ii] The value of interfacial tension is calculated by relational expression (1) or relational expression (6) above from the surface tensions of 10 brands of semicoke which are prepared respectively from the 10 brands of coal and the proportions of the 10 brands of coal to the whole coal stock. In relational expression (3) and relational expression (7), blending ratio $w_i$ is equal to the abundance ratio of each brand of coal in the coal stock.

[1iii] Using the value of the surface tension of each semicoke which is prepared from each of the brands of coal selected in process [1i] above which is decided so that the value of the interfacial tension calculated in process [1ii] above is 0.03 mN/m or lower as a control value, the weathering degree of the control target brand of coal is controlled so that the value of the surface tension is preferably not equal to or lower than the control value.

Controlling Method (2)

[2i] One brand (control target brand) of coal whose weathering degree is to be controlled is selected from among plural brands of coal included in coal stock.

[2ii] The weighted average of surface tensions of brands of semicoke which are prepared from the remaining brands of coal other than the control target brand of coal selected in [2i] above among the plural brands of coal weighted by the proportions of the remaining brands of coal is calculated.

[2iii] The weathering degree of the control target brand of coal is controlled so that the difference in surface tension between the weighted average value and the value of the surface tension of the semicoke which is prepared from the control target brand of coal may be 1.5 mN/m or lower.

Controlling Method (3)

The weathering degree of a control target brand of coal is controlled so that the semicoke which is prepared by performing a heat treatment on the control target brand of coal has a surface tension of 39.5 mN/m or higher, the value of 39.5 mN/m is the surface tension of the semicoke which is prepared by performing a heat treatment at a temperature of 500° C. on the weathered coal. Although it is appropriate to control the weathering degree so that the surface tension is 39.5 mN/m or higher in the case where the surface tension of the semicoke which is prepared by performing a heat treatment at a temperature of 500° C. is determined and controlled, it is not necessary to limit the heat treatment temperature to 500° C. However, since the surface tension of semicoke varies depending on the preparation temperature of the semicoke for the same coal, the control value of the surface tension of semicoke is preferably a value equivalent to 39.5 mN/m in terms of the surface tension of the semicoke which is prepared by performing a heat treatment at a temperature of 500° C. in the case where the surface tension of the semicoke which is prepared by performing a heat treatment at a temperature different from 500° C. is used for the control. In the case where semicoke is prepared at a temperature different from 500° C., it is judged by using, specifically, process [A] and [B] and/or [C] below whether or not the semicoke which is prepared from the weathered control target brand of coal has a surface tension equivalent to the preferable value of 39.5 mN/m or higher described above.

In a practical operation, there are plural brands of coal as targets for controlling the weathering degree. First, processes [A] through [C] will be described hereafter under the assumption, in the below examples, that the process [A] and the process [B] and/or [C] below are performed on one of all such brands of coal.

[A] For example, the surface tension of the semicoke which is prepared from each of the various brands of coal for producing coke including weathered brands of coal is determined for various heat treatment temperatures. With this, the relationship between a heat treatment temperature and the surface tension of semicoke (surface tension corresponding to the heat treatment temperature) which is prepared by performing a heat treatment at the heat treatment temperature is clarified for various brands of coal. Correlation curves between a heat treatment temperature and surface tension corresponding to the heat treatment temperature are produced based on the relationship mentioned above for various kinds of semicoke which are prepared from various kinds of coal in various weathered states.

[B] Semicoke is prepared by performing a heat treatment at some temperature on some amount of some brand of coal under control in some weathered state, and the surface tension of the semicoke is determined. A correlation curve which gives the value equal to the determined surface tension for the used heat treatment temperature may be selected from among the correlation curves described above. By using the value which is given by the selected correlation curve for a heat treatment temperature of 500° C., it is possible to estimate the surface tension of the semicoke which is prepared by performing a heat treatment at a temperature of 500° C. on the used coal. In the case where the estimated surface tension is 39.5 mN/m or higher, it is possible to determine that the semicoke which is prepared from the coal in some weathered state has a surface tension equivalent to or higher than 39.5 mN/m.

[C] Semicoke is prepared by performing a heat treatment at some temperature on some amount of some brand of coal under control in some weathered state, and the surface tension of the semicoke is determined. Correlation curves which give a surface tension of 39.5 mN/m or higher for a heat treatment temperature of 500° C. are selected from among the correlation curves obtained in process [A] above. The minimum value for surface tension among the values which are given for the used heat treatment temperature by one or plural selected correlation curves is found. In the case where the determined surface tension is equal to or higher than the found minimum preferable value, it is possible to determine that the semicoke which is prepared from the coal in some weathered state has a surface tension equivalent to or higher than 39.5 mN/m.

Process [C] above may be performed in combination with or instead of process [B] above. In the case where the relationship between the weathering condition of some coal (for example, a storage period in a stock yard alone or coupled with climate conditions during storage, or the like) and the surface tension of the semicoke which is prepared from the coal at a temperature of, for example, 500° C. is obtained in advance, since it is possible to estimate surface tension in accordance with practical weathering condition, the estimated value may be used for control.

By performing processes [A] and ([B] and/or [C]) above on all the control target brands of coal, in the case of each of the control target brands of coal, it is possible to determine whether or not the semicoke which is prepared from the coal has a surface tension of 39.5 mN/m or higher. The value 39.5 mN/m is the surface tension of the semicoke which is prepared by performing a heat treatment at a temperature of 500° C. on the weathered coal.

From the results of investigations performed on many kinds of coal which are normally used in a coke factory in a steel plant, in the case where the semicoke which is prepared from weathered coal has a surface tension of 39.5 mN/m or higher in terms of the surface tension of the semicoke which is prepared by performing a heat treatment at a temperature of 500° C. on the weathered coal, it is possible to add the weathered coal to a coal blend without decreasing the strength of coke. Therefore, by using the surface tension of semicoke as an index, in the case where the surface tension is lower than the value equivalent to 39.5 mN/m, this case is determined to be a case of excessive weathering, and the weathering degree of coal is controlled so that surface tension of the semicoke which is prepared from the coal is not lower than the value equivalent to 39.5 mN/m and the weathering may be suppressed.

By changing the selected brand of coal to another brand among the remaining nine brands of coal by turn in processes [1i] and [2i] above, it is possible to control the weathering degrees of all the brands of coal included in the coal stock. In order to operate controlling methods (1) through (3) above, it is preferable that the surface tension of each semicoke which is prepared from each of all the brands of coal in a stock yard be determined periodically, for example, once or more a month. Since weathering rate varies depending on the brand of coal, it is acceptable that the surface tension of a brand of semicoke having a low weathering rate be determined with lower frequency, that the surface tension of a brand of semicoke having a high weathering rate be determined with higher frequency, and that weathering degree be controlled based on the brand of coal having a high weathering rate.

By using exemplary controlling methods (1) through (3) above, coal stock in a stock yard may be controlled so that the semicoke which is prepared from the coal included in the coal stock has a chemical composition that always realizes the surface tension of an average preferable value and so that it is possible to avoid a situation in which a large amount of weathered coal, which causes a decrease in strength, is stored. Moreover, by assessing the weathering degree of coal, it is possible to add weathered coal to a coal blend without the occurrence of a decrease in the strength of coke which has been unpredictable to date.

Example 1

The method for evaluating the weathering degree of coal in which the weathering degree of weathered coal is evaluated by using the surface tension of the semicoke which is prepared by performing a heat treatment on the weathered coal as an index was tried and verified. First, coal F and coals G through M were provided, and a part of coal F was subjected to intentionally accelerated weathering. The interfacial tension $\gamma_{inter}$ of a semicoke blend which is prepared from a coal mixture which was composed of these kinds of coal with certain blending ratios was determined.

As is the case with the experiment described above, weathered kinds of coal which were subjected to weathering by heating coal F at a temperature of 150° C. for 1 hour, 5 hours, 6 hours, and 10 hours in the air are respectively called as weathered coal of coal $F_1$, coal $F_2$, coal $F_3$, and coal $F_4$. The coal which was not subjected to a heat treatment is called coal $F_0$ as un-weathered coal. The properties of each of these coals (weathered coal) and the semicoke which is prepared from each of these coals are given in Table 2.

TABLE 2

| Coal Name | γ [mN/m] | Ro [—] | MF [logddpm] | Ash [%, d.b.] | VM [%, d.b.] |
|---|---|---|---|---|---|
| Coal $F_0$ | 40.7 | 0.95 | 3.00 | 7.9 | 28.8 |
| Coal $F_1$ | 40.3 | 0.95 | 1.49 | | |
| Coal $F_2$ | 39.6 | 0.95 | 0.85 | | |
| Coal $F_3$ | 39.4 | 0.95 | 0.70 | | |
| Coal $F_4$ | 39.0 | 0.95 | 0.00 | | |

The properties of the brands of coal which were used in EXAMPLE 1 are given in Table 3.

TABLE 3

| Coal Name | γ [mN/m] | Ro [—] | MF [logddpm] | Ash [%, d.b.] | VM [%, d.b.] |
|---|---|---|---|---|---|
| Coal G | 41.3 | 0.72 | 3.03 | 9.7 | 38.1 |
| Coal H | 43.7 | 0.79 | 3.96 | 7.9 | 37.2 |
| Coal I | 42.2 | 0.91 | 3.64 | 7.9 | 33.4 |
| Coal J | 40.7 | 1.03 | 3.09 | 9.1 | 27.8 |
| Coal K | 41.0 | 1.37 | 1.04 | 7.0 | 19.3 |
| Coal L | 39.5 | 1.44 | 2.03 | 9.3 | 21.1 |
| Coal M | 37.7 | 1.62 | 0.70 | 9.5 | 18.8 |

In Table 2 and Table 3, each semicoke was prepared from each brand of coal by the above processes (a') through (d'). Mean maximum reflectance Ro of vitrinite in coal was determined in accordance with JIS M 8816, maximum fluidity MF was determined in accordance with JIS M 8801, and ash (Ash) and volatile matter (VM) were determined in accordance with JIS M 8812. The determined values are given in Table 2 and Table 3. Maximum fluidity MF (ddpm) is indicated in Table 2 and Table 3 in terms of the common logarithm of MF (log MF). Surface tension γ [mN/m] is the value of the surface tension of the semicoke which is prepared from the coal named in "Coal Name" column. The value for the surface tension was derived as the average value of the surface tension distribution which was obtained by using a film flotation method as described above.

Coke was produced from a coal mixture which was composed of coals $F_0$ through $F_4$ given in Table 2 and coals G through M given in Table 3 with appropriate blending ratios, and the strength of the coke was determined. The blending ratios of the constituent kinds of coal of the coal mixture and the properties of each coal blend are given in Table 4.

TABLE 4

| Blend Name | | Coal $F_0$ Blend | Coal $F_1$ Blend | Coal $F_2$ Blend | Coal $F_3$ Blend | Coal $F_4$ Blend |
|---|---|---|---|---|---|---|
| Blending Ratio [%] | Coal $F_0$ | 20 | 0 | 0 | 0 | 0 |
| | Coal $F_1$ | 0 | 20 | 0 | 0 | 0 |
| | Coal $F_2$ | 0 | 0 | 20 | 0 | 0 |
| | Coal $F_3$ | 0 | 0 | 0 | 20 | 0 |
| | Coal $F_4$ | 0 | 0 | 0 | 0 | 20 |
| | Coal G | 33 | 13 | 11 | 6 | 0 |
| | Coal H | 0 | 0 | 0 | 1 | 5 |
| | Coal I | 0 | 21 | 21 | 22 | 33 |
| | Coal J | 11 | 19 | 23 | 28 | 19 |
| | Coal K | 26 | 20 | 14 | 15 | 11 |
| | Coal L | 5 | 4 | 11 | 8 | 12 |
| | Coal M | 5 | 3 | 0 | 0 | 0 |
| Ro of Coal Mixture [-] | | 1.05 | 1.05 | 1.05 | 1.05 | 1.05 |
| MF of Coal Mixture [logddpm] | | 2.35 | 2.35 | 2.35 | 2.34 | 2.34 |
| $\gamma_{inter1}$ [mN/m] | | 0.021 | 0.027 | 0.030 | 0.035 | 0.062 |
| $\gamma_{inter2}$ [mN/m] | | 0.021 | 0.027 | 0.030 | 0.035 | 0.062 |
| Weighted Average [mN/m] | | 40.8 | 41.1 | 41.1 | 41.1 | 41.4 |
| Difference from Weighted Average [mN/m] | | 0.1 | 0.8 | 1.5 | 1.7 | 2.4 |
| DI150/15 [-] | | 82.3 | 82.2 | 82.2 | 81.2 | 79.9 |
| CSR [%] | | 54.1 | 54.0 | 53.7 | 51.1 | 48.7 |

Ro and log MF of a coal mixture given in Table 4 are the conditions used in the mixture of a practical operation, and it is known that the strength of coke is fundamentally constant for constant Ro and log MF according to a knowledge based on conventional coal blending. The values of Ro and log MF are respectively the weighted average values of these properties of the constituent kinds of coal of the coal mixture weighted by the blending ratios of the constituent kinds of coal. Interfacial tension $\gamma_{inter1}$ was calculated by relational expression (1) from the surface tensions of the plural kinds of semicoke which are prepared from the plural brands of coal included in the coal mixture and the blending ratios of the constituent kinds of coal included in the coal mixture. $\gamma_{inter2}$ is the value of the interfacial tension of semicoke calculated by relational expression (6) as is the case with relational expression (1). In addition, the weighted average value of the surface tensions of the kinds of semicoke which are prepared from the remaining brands of coal other than coal F or weathered coal F included in the coal mixture weighted by the blending ratios of the remaining brands of coal (for descriptive purposes, also called "weighted average"), and the difference between the weighted average and the surface tension of coal F or weathered coal F are also given in Table 4.

Coke was produced by carbonizing the coal mixture which was composed of the constituent kinds of coal with the blending ratios given in Table 4, and the strength of the coke was determined. 16 kg of the coal mixture controlled to have coal particles having a diameter of 3 mm or less of 100 mass % and a humidity of 8 mass % was compacted to the bulk density of 750 kg/m$^3$ and then carbonized in an electric furnace. After carbonization had been performed at a heating wall temperature was 1100° C. for 6 hours, nitrogen cooling was performed in order to obtain coke. The strength of coke was evaluated by using a drum strength index DI150/15 based on a drum strength test method in accordance with JIS K 2151 and coke strength after $CO_2$ reaction CSR based on ISO 18894. The values of DI150/15 and CSR are given in Table 4.

Figure 2:
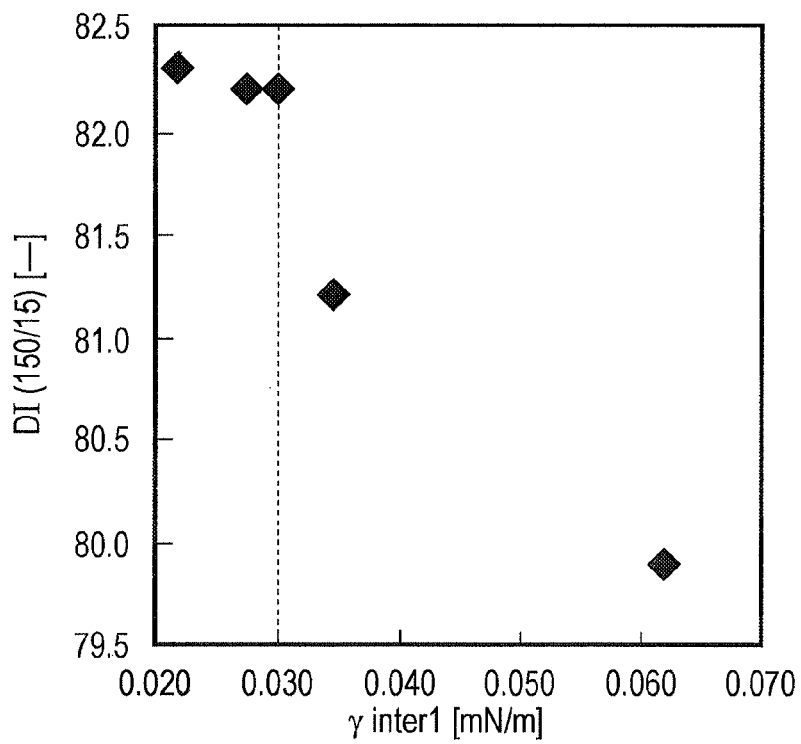
FIG. 2 shows a graph illustrating the relationship, in EXAMPLE 1, between the interfacial tension of a semicoke blend and the strength of coke which is obtained by carbonizing a coal blend.
Figure 3:
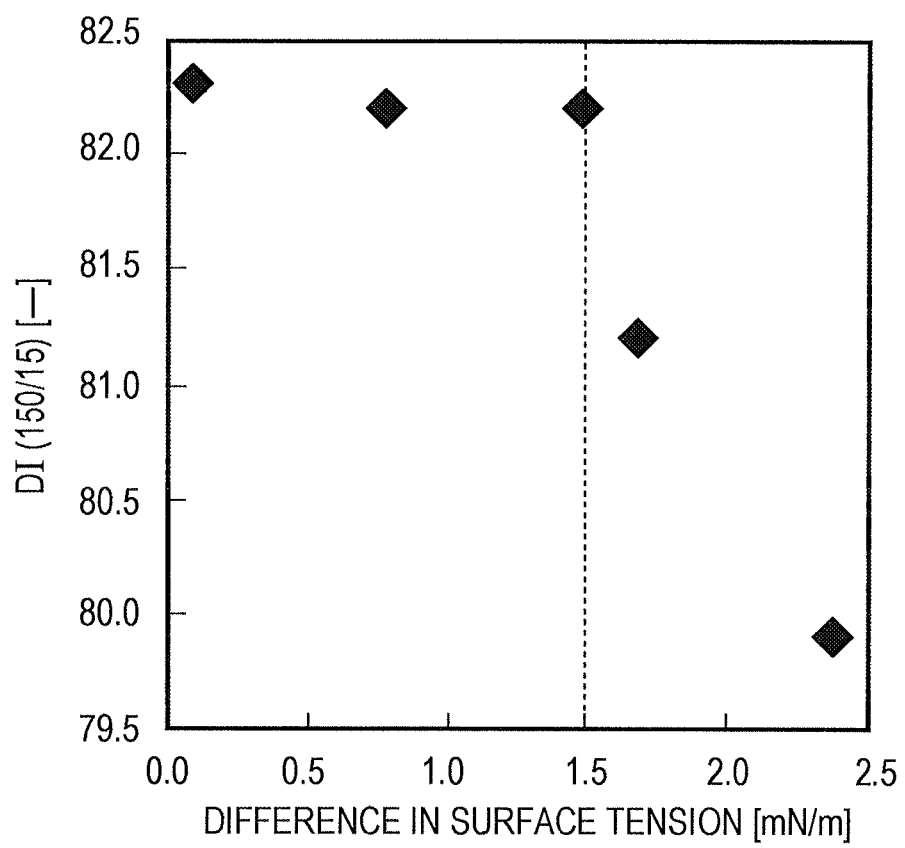
FIG. 3 shows a graph illustrating the relationship, in EXAMPLE 1, between the difference between the surface tension of the semicoke which is prepared from a control target brand of coal and the weighted average value of surface tensions of the brands of semicoke which are prepared from the remaining brands of coal and the strength of coke which is obtained by carbonizing a coal blend.

Based on a comparison between the case where coal $F_0$ was added and the case where coal $F_3$ or coal $F_4$ was added in EXAMPLE 1, as Table 4 indicates, it is clarified that there is a case where a decrease in the strength of coke occurs in the case where weathered coal is added even if satisfactory values for the Ro and log MF of a coal mixture are maintained. While the strength of coke equivalent to that in the case where coal $F_0$ which is not weathered is added is maintained in the case where coal $F_1$ or coal $F_2$ is added, there is a decrease in the strength of coke in the case where coal $F_3$ or coal $F_4$, which is weathered more than coal $F_2$ is added to the coal mixture. This fact indicates that, it is possible to use weathered coal without decreasing strength by controlling interfacial tension and differences of surface tension to be within a preferable range even in the case where weathered coal is added. In this case, the preferable range for interfacial tension was 0.03 mN/m or less, and the difference between the weighted average value of the surface tensions of the kinds of semicoke which was prepared from the remaining kinds of coal other than the weathered coal and the surface tension of the semicoke which was prepared from the weathered coal was 1.5 mN/m or less. FIG. 2 illustrates the relationship between interfacial tension $\gamma_{inter1}$ and drum strength index DI150/15, and FIG. 3 illustrates the relationship between the difference from the weighted average value and drum strength index DI150/15. As graphs of FIG. 2 and FIG. 3 indicate, it is clarified that the strength of coke significantly changes at a point for an interfacial tension $\gamma_{inter1}$ of 0.03 mN/m and at a point for a difference from the weighted average value of 1.5 mN/m.

Figure 4:
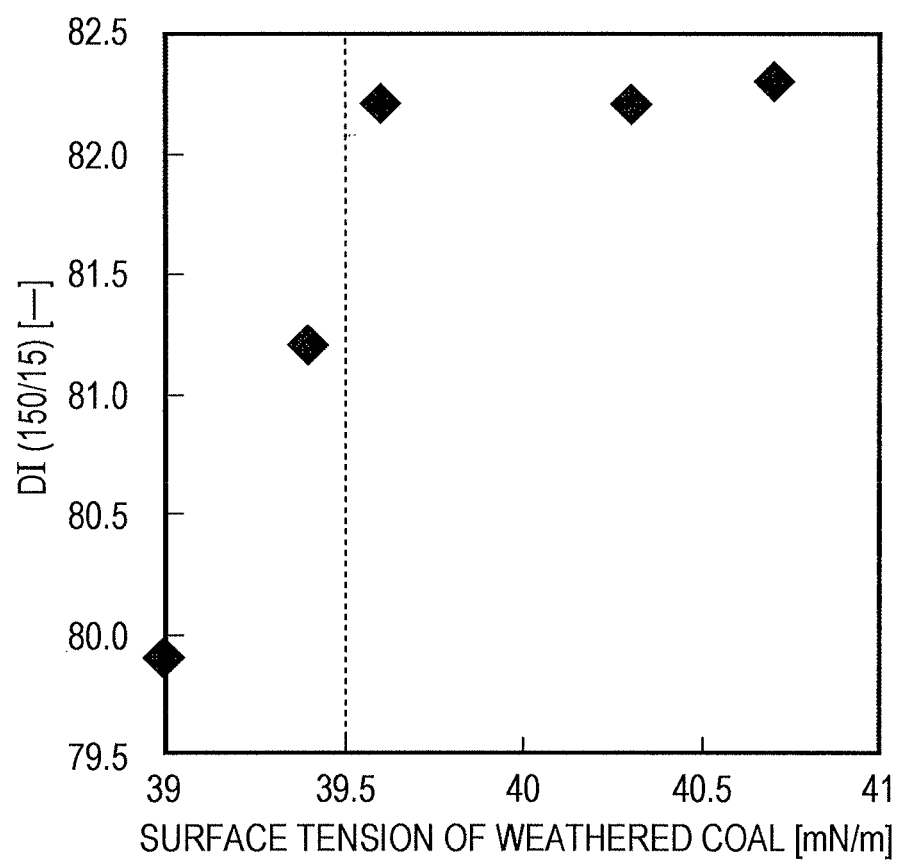
FIG. 4 shows a graph illustrating the relationship, in EXAMPLE 1, between the surface tension of the semicoke which is prepared from a control target brand of coal and the strength of coke which is obtained by carbonizing a coal blend.

In addition, by referring to Table 2 in combination with Table 4, while the surface tension of the semicoke which was prepared from coal $F_1$ or $F_2$ is 39.5 mN/m or higher, the surface tension of the semicoke which was prepared from coal $F_3$ or $F_4$ is less than 39.5 mN/m. FIG. 4 illustrates the relationship between the surface tension of semicoke and drum strength index DI150/15. As the graph of FIG. 4 indicates, it is clarified that the strength of coke significantly changes at a point for a surface tension of semicoke of 39.5 mN/m and that it is possible to use weathered coal without decreasing strength in the case where the surface tension of the semicoke which is prepared from weathered coal is 39.5 mN/m or higher even if weathered coal is added to a coal blend.

From the results described above, it is clarified that, by controlling the surface tension of the semicoke which is prepared by performing a heat treatment on weathered coal to be within the preferable range described above, it is possible to add weathered coal to a coal blend, which is a raw material for coke, without decreasing strength.

Moreover, in the case where coke is produced by using weathered coal, by evaluating the weathering degree of the coal by using the surface tension of semicoke as an index, and by controlling the weathering degree of stored coal to be within a control range (the range for the surface tension of semicoke described above), it is possible to effectively prevent a decrease in the strength of coke due to the weathering of coal on average over the long term even though the blending ratios of brands of coal for producing coke and the abundance ratio of the brands of coal in the coal stock are not always the same.

In the case where the properties of coal are controlled without using the method for evaluating the weathering degree of coal according to aspects of the present invention, for example, in the case where the weathering degree of stored coal is not controlled or in the case where an index of weathering degree whose influence on the strength of coke is not clear is used, there is a case where coal having an excessive weathering degree is stored. In such a case, the weathered coal is used for a coal blend on some occasion, which results in an unexpected decrease in the strength of coke. By using the method for evaluating the weathering degree of coal according aspects of the present invention, since it is possible to control the qualities of stored coal so that coal having an excessive weathering degree is not stored, it is possible to produce coke having a stable strength.

Example 2

A semicoke sample was prepared from each of coal N and coal O with various heat treatment temperatures by using the same method as used in EXAMPLE 1, and the surface tension of the semicoke was determined. The results of the determination are given in Table 5.

TABLE 5

| | Heat Treatment Temperature (° C.) | | | | | |
|---|---|---|---|---|---|---|
| | 350 | 400 | 450 | 500 | 600 | 800 |
| Surface Tension of Semicoke (Coal N) [mN/m] | 31.9 | 33.0 | 35.5 | 41.1 | 45.2 | 52.3 |
| Surface Tension of Semicoke (Coal O)[mN/m] | 29.8 | 30.4 | 32.4 | 37.6 | 42.2 | 48.7 |

As Table 5 indicates, it is clarified that, in a temperature range of 350° C. or higher, there is a tendency for the value of surface tension to increase with increasing heat treatment temperature. However, the difference between the surface tensions of the two kinds of semicoke for the same heat treatment temperature is almost constant, that is, the magnitude relationship between the surface tensions of different kinds of semicoke which are prepared from different kinds of coal does not change depending on the change in the temperature at which semicoke is prepared. Therefore, it is preferable that a heat treatment temperature at which semicoke is prepared be 350° C. or higher and 800° C. or lower in the method according to an embodiment of the present invention. Here, in consideration of such heat treatment temperature dependency of surface tension, it is preferable that the surface tension of semicoke be evaluated by performing a heat treatment on all the control target brands of coal substantially at the same heat treatment temperature.

The invention claimed is:

1. A method for evaluating a weathering degree of coal comprising:
   using surface tension of semicoke which is prepared by performing a heat treatment on a weathered coal as an index for evaluating the weathering degree, wherein the heat treatment is performed at a temperature equal to or higher than 350° C. and equal to or lower than 800° C. on the weathered coal and then the weathered coal is cooled in an atmosphere sealed from air or in an atmosphere of an inert gas.

2. A method for evaluating a coking property of weathered coal when coke is produced from coal blend including the weathered coal comprising:
   using surface tension of semicoke which is prepared by performing a heat treatment on the weathered coal as an index for evaluating an amount of decrease in a strength of the coke due to weathering, wherein the heat treatment is performed at a temperature equal to or higher than 350° C. and equal to or lower than 800° C. on the weathered coal and then the weathered coal is cooled in an atmosphere sealed from air or in an atmosphere of an inert gas.

3. A method for controlling a weathering degree of coal by using the method according to claim 1 comprising steps of:
   determining surface tension of each brand of semicoke which is prepared by performing a heat treatment on each of plural brands of coal included in coal stock and assessing a proportion of each of the plural brands of coal in the coal stock; and
   in a condition the plural brands of semicoke are blended in accordance with the respective proportions to prepare a semicoke blend, controlling the weathering degree of each of the plural brands of coal so that a value of interfacial tension $\gamma_{inter}$ of the semicoke blend which is derived from the surface tensions and the proportions is 0.03 mN/m or lower.

4. A method for controlling a weathering degree of coal by using the method according to claim 1 comprising steps of:
   determining surface tension of each brand of semicoke which is prepared by performing a heat treatment on each of plural brands of coal included in coal stock and assessing a proportion of each of the plural brands of coal in the coal stock; and
   controlling the weathering degree of a control target brand of coal included in the coal stock so that a difference $\Delta\gamma$ in surface tension regarding a semicoke is 1.5 mN/m or lower, the difference $\Delta\gamma$ being between value of surface tension of the semicoke which is prepared by performing a heat treatment on the control target brand of coal and weighted average value which is calculated by weighted averaging surface tensions of the brands of semicoke which are prepared by performing a heat treatment on remaining brands of coal other than the control target brand of coal included in the coal stock according to proportions of the remaining brands of coal.

5. A method for controlling a weathering degree of coal by using the method according to claim 1 comprising:
   controlling the weathering degree of a control target brand of coal so that a semicoke which is prepared from the weathered control target brand of coal has surface tension corresponding to 39.5 mN/m or higher, the value 39.5 mN/m being surface tension of the semicoke which is prepared by performing a heat treatment at a temperature of 500° C. on the weathered brand of coal.

6. A method for producing coke comprising steps of:
   preparing a coal blend by blending the brands of coal whose weathering degrees have been controlled by using the methods according to claim 3; and
   producing coke by carbonizing the coal blend.

7. A method for producing coke comprising steps of:
   preparing a coal blend by blending the brands of coal whose weathering degrees have been controlled by using the methods according to claim 4; and
   producing coke by carbonizing the coal blend.

8. A method for producing coke comprising steps of:
   preparing a coal blend by blending the brands of coal whose weathering degrees have been controlled by using the methods according to claim 5; and
   producing coke by carbonizing the coal blend.

* * * * *